United States Patent

Zhou et al.

[11] Patent Number: 5,889,184
[45] Date of Patent: Mar. 30, 1999

[54] PROCESS FOR PYRIMIDINONE COMPOUNDS

[75] Inventors: Ping Zhou, Plainsboro; Edward Curtis Taylor, Princeton, both of N.J.; Colin Michael Tice, Elkins Park, Pa.

[73] Assignees: Princeton University, Princeton, N.J.; Rohm and Haas Company, Philadelphia, Pa.

[21] Appl. No.: 831,174

[22] Filed: Apr. 2, 1997

Related U.S. Application Data

[60] Provisional application No. 60/015,244 Apr. 10, 1996.

[51] Int. Cl.$^6$ ........................ C07D 239/36; C07D 239/52
[52] U.S. Cl. ........................................ 544/319; 544/229
[58] Field of Search ...................................... 544/319, 229

[56] References Cited

PUBLICATIONS

Chemical Abstracts, vol. 60, 9276d (1964).
Chemical Abstracts, vol. 59, 11524h (1963).

*Primary Examiner*—John M. Ford
*Attorney, Agent, or Firm*—Clark R. Carpenter

[57] ABSTRACT

This invention relates to a process for the preparation of pyrimidinone compounds of the formula

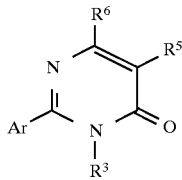

wherein Ar is an optionally substituted aryl or heteroaromatic moiety, $R^3$ is an optionally substituted alkyl, alkenyl or alkynyl, $R^5$ is a hydrogen atom, halo, cyano or an optionally substituted alkyl, alkenyl, alkynyl, alkoxy or alkylthio, and $R^6$ is a hydrogen atom, cyano, or an optionally substituted alkyl, cycloalkyl, alkenyl, alkynyl, aryl, aralkyl or heteroaryl.

The process comprises reaction of an amidine and a malonic acid derivative to give a hydroxypyrimidinone followed by conversion of the resulting hydroxypyrimidinone to a sulfonyloxypyrimidinone followed by reaction of the resulting sulfonyloxypyrimidinone with an organometallic reagent to give the desired pyrimidinone. The hydroxypyrimidinones, wherein $R^6$ is hydroxy and sulfonyloxypyrimidinones wherein $R^6$ is a substituted sulfonyloxy moiety, are themselves new and useful intermediates in the preparation of the desired pyrimidinones.

25 Claims, No Drawings

PROCESS FOR PYRIMIDINONE COMPOUNDS

This is a nonprovisional application of prior pending provisional application Ser. No. 60/015,244 filed Apr. 10, 1996

This invention relates to a process for the preparation of pyrimidinone compounds. The process comprises reaction of an amidine and a malonic acid derivative to give a hydroxypyrimidinone followed by conversion of the resulting hydroxypyrimidinone to a sulfonyloxypyrimidinone followed by reaction of the resulting sulfoinyloxypyrimidinone with an organometallic reagent to give the desired pyrimidinone. The pyrimidinone compounds produced by the process of the present invention are very useful as herbicidal agents for the control of weeds in agronomically important crops. Such uses are disclosed in both U.S. Pat. No. 5,300,477 and U.S. Pat. No. 5,453,414.

Existing art for preparation of certain pyrimidinone herbicides of formula V

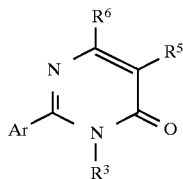

requires alkylation, for example, propargylation, of a pyrimidinone of formula V when $R^3$ is a hydrogen atom and gives a mixture of N- and O-alkylation (propargylation) products that are difficult to separate. Often the undesired O-alkylated (propargylated) product predominates. The method of the present invention completely avoids this selectivity problem through the use of a different chemical process.

One of the intermediates of formula III in the process of this invention is

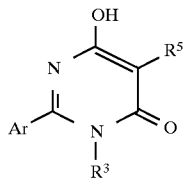

disclosed in both *Chem. Abstr.* 60: 9276d and *Chem. Abstr.* 59: 11524h wherein Ar is phenyl, $R^3$ is ethyl and $R^5$ is a hydrogen atom. However, the process used in both these references employs the reaction of carbon suboxide with N-ethylbenzamidine. The references neither disclose nor suggest the process of the present invention.

One embodiment of the process of the present invention to make a pyrimidinone compound of formula V

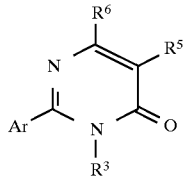

comprises the steps of
(i) reacting an N-substituted amidine of formula I with an activated malonic acid derivative of formula II at room temperature or below in the presence of a base and a solvent or solvent mixture to form a hydroxypyrimidinone compound of formula III

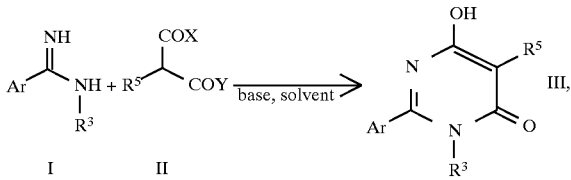

(ii) reacting the resulting hydroxypyrimidinone compound of formula III with a compound of the formula $RfSO_2Z$ to form a sulfonyloxypyrimidinone compound of formula IV

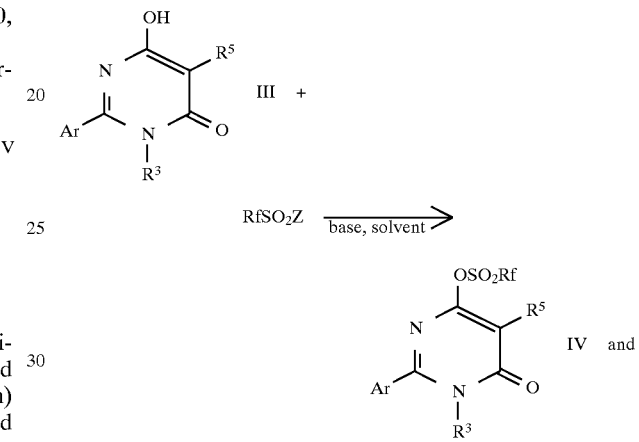

(iii) reacting the resulting sulfonyloxypyrimidinone compound of formula IV with an organometallic reagent of the formula $R^6M$, in the presence or absence of catalysts, a base and other additives, at a temperature from about −80° C. to about 150° C. in a solvent or mixture of solvents to form a pyrimidinone compound of formula V wherein Ar is a $(C_6-C_{10})$aryl or $(C_4-C_5)$heteroaromatic group, or a $(C_6-C_{10})$aryl or $(C_4-C_5)$heteroaromatic group substituted with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_{12})$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, alkylenedioxy and nitro;

$R^3$ is a $(C_1-C_6)$alkyl, $(C_3-C_6)$alkenyl, $(C_3-C_6)$alkynyl, $(C_1-C_6)$alkoxy$(C_2-C_6)$alkyl, or silyl$(C_3-C_6)$alkynyl of the form $(CH_2)_n C\equiv\!\!-CSiR^a R^b R^c$ wherein n is 1, 2, 3 or 4 and $R^a$, $R^b$, and $R^c$ are independently selected from $(C_1-C_6)$alkyl and phenyl; or is a $(C_1-C_6)$alkyl, $(C_3-C_6)$alkenyl, $(C_3-C_6)$alkynyl, $(C_1-C_6)$alkoxy$(C_2-C_6)$alkyl, or silyl$(C_3-C_6)$alkynyl of the form $(CH_2)_n C\equiv\!\!CSiR^a R^b R^c$ wherein n is 1, 2, 3 or 4 and $R^a$, $R^b$, and $R^c$ are independently selected from $(C_1-C_6)$alkyl and phenyl, wherein each of the foregoing groups is substituted with up to five halogen atoms;

$R^5$ is a hydrogen atom, $(C_1-C_6)$alkyl, $(C_3-C_6)$alkenyl, $(C_3-C_6)$alkynyl, $(C_1-C_6)$alkoxy, halo$(C_1-C_6)$alkyl, halo$(C_2-C_6)$alkenyl, halo$(C_2-C6)$alkynyl, halo$(C_1-C_6)$alkoxy, $(C_1-C_6)$alkylthio, a halogen atom or cyano;

$R^6$ is a hydrogen atom, $(C_1-C_{12})$alkyl, cyclo$(C_3-C_7)$alkyl, $(C_2-C_2)$alkenyl, $(C_2-C_{12})$alkynyl, halo$(C_1-C_6)$alkyl, halo$(C_2-C_6)$alkenyl, halo$(C_2-C_6)$alkynyl, tri$(C_1-C_6)$alkylsilyl$(C_2-C_{12})$alkynyl, cyano, $(C_6-C_{10})$aryl, ar$(C_1-C_4)$alkyl, $(C_4-C_5)$heterocyclyl, or $(C_6-C_{10})$aryl, ar$(C_1-C_4)$alkyl or $(C_4-C_5)$heterocyclyl substituted on the aryl portion with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, and nitro;

X and Y are both good leaving groups;

Z is fluoro, chloro or $OSO_2Rf$;

Rf is perfluoro$(C_1-C_{12})$alkyl or fluoro; and $R^6M$ is an organometallic reagent wherein M is selected from lithium, copper, aluminum, magnesium, zinc, tin, silicon, boron and combinations thereof.

The groups such as alkyl, alkenyl, alkynyl, alkoxy, alkylthio and the like as well as other moieties containing these groups, such as aralkyl, alkoxyalkyl, alkylsulfonyl and the like, described hereinabove and below can be either a straight chain such as n-propyl or a branched chain such as isobutyl or tert-butyl. The prefix halo in such groups, such as haloalkyl, haloalkoxy and the like, can represent monohalo, polyhalo in which the halogen atoms can be the same or different, or perhalo.

In a preferred embodiment, the process of the present invention leading to a pyrimidinone compound of formula V comprises the steps of (i) reacting an N-substituted amidine of formula I with an activated malonic acid derivative of formula II from about $-40°$ C. to about $-80°$ C. in the presence of an amine or an amide base and an ether, hydrocarbon, chlorinated hydrocarbon or a nitrile solvent or a mixture thereof to form a hydroxypyrimidinone compound of formula III, (ii) reacting the resulting hydroxypyrimidinone compound III with a compound of the formula $RfSO_2Z$ to form a sulfonyloxypyrimidinone compound of formula IV and (iii) reacting the resulting sulfonyloxypyrimidinone compound of formula IV with an organometallic reagent of the formula $R^6M$, in the presence or absence of catalysts, a base and other additives, at a temperature from about $-80°$ C. to about $150°$ C. in a solvent or a mixture of solvents to form a pyrimidinone compound of formula V wherein Ar is furyl, naphthyl, phenyl, pyridyl, pyridyl salt or thienyl, or furyl, naphthyl, phenyl, pyridyl, pyridyl salt or thienyl substituted with up to three substituents independently selected from bromo, chloro, fluoro, $(C_1-C_6)$alkyl, cyclo$(C_5-C_6)$alkyl, $(C_2-C_6)$alkenyl, cyclo$(C_3-C_8)$alkenyl, $(C_2-C_6)$alkynyl, halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_6)$alkoxy, 1,3-dioxalan-2-yl, methylenedioxy, 1,2-ethylenedioxy and nitro;

$R^3$ is methyl, ethyl, n-propyl, $(C_3-C_4)$alkenyl, $(C_3-C_6)$alk-2-ynyl, $(C_1-C_2)$alkoxy$(C_2-C_3)$alkyl, 3-(trimethylsilyl)prop-2-ynyl, 3-(tert-butyldimethylsilyl)prop-2-ynyl or 3-(phenyldimethylsilyl)prop-2-ynyl, or is methyl, ethyl, n-propyl, $(C_3-C_4)$alkenyl, $(C_3-C_6)$alk-2-ynyl, $(C_1-C_2)$alkoxy$(C_2-C_3)$alkyl, 3-(trimethylsilyl)prop-2-ynyl, 3-(tert-butyldimethylsilyl)prop-2-ynyl or 3-(phenyldimethylsilyl)prop-2-ynyl wherein each of the foregoing groups is substituted with up to five halogen atoms;

$R^5$ is a hydrogen atom, chloro, fluoro, methyl, ethyl, n-propyl, isopropyl, allyl, prop-2-ynyl, $(C_1-C_2)$alkoxy, $C_1-C_2)$alkylthio, halo$(C_1-C_2)$alkyl or halo$(C_1-C_2)$alkoxy;

$R^6$ is a hydrogen atom, $(C_1-C_6)$alkyl, cyclopropyl, cyclobutyl, cyclopentyl, $(C_2-C_6)$alkenyl, $(C_2-C_6)$alkynyl, halo$(C_1-C_3)$alkyl, halo$(C_2-C_6)$alkenyl, halo$(C_2-C_6)$alkynyl, tri$(C_1-C_6)$alkylsilyl$(C_2-C_{12})$alkynyl, cyano, phenyl, benzyl, 2-furyl, 3-furyl, 2-thienyl, 3-thienyl, 2-pyridyl, 3-pyridyl or 4-pyridyl, or phenyl, benzyl, 2-furyl, 3-furyl, 2-thienyl, 3-thienyl, 2-pyridyl, 3-pyridyl or 4-pyridyl substituted on the aryl portion with up to three substituents independently selected from bromo, fluoro, fluoro, $(C_1-C_6)$alkyl, cyclo$(C_5-C_6)$alkyl, $(C_2-C_6)$alkenyl, cyclo$(C_3-C_8)$alkenyl, $(C_2-C_6)$alkynyl, halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_6)$alkoxy, 1,3-dioxalan-2-yl and nitro;

X and Y are independently selected from chloro, carboxylate and 1-imidazolyl;

Z is fluoro, chloro or $OSO_2Rf$;

Rf is perfluoro$(C_1-C_4)$alkyl or fluoro; and $R^6M$ is an organometallic reagent selected from $(R^6)_2CuCNLi_2$, $(R^6)_3B$ and $R^6SnR^xR^yR^z$ wherein $R^x$, $R^y$ and $R^z$ are alkyl.

In step (i) of this preferred embodiment, preferred bases are triethylamine, N-methylmorpholine, lithium diisopropylamide and sodium bis(trimethylsilyl)amide. The most preferred base is sodium bis(trimethylsilyl)amide. Preferred solvents are tetrahydrofuran (THF), diethyl ether, dioxane, dimethoxymethane, toluene, dichloromethane and acetonitrile. THF is the most preferred solvent.

In step (ii) of this preferred embodiment, trifluoromethanesulfonic anhydride is a preferred reactant to convert a hydroxypyrimidinone compound of formula III to a sulfonyloxypyrimidinone compound of formula IV.

In step (iii) of this preferred embodiment, when the organometallic reagent is a higher order cuprate such as $(R^6)_2CuCNLi_2$, no catalyst is employed and preferred temperatures are from about $-80°$ C. to about $-40°$ C. and THF is a preferred solvent. When the organometallic reagent is a borane or tin compound, preferred catalysts include palladium and nickel compounds such as tetrakis(triphenylphosphine)palladium[0], [1,1'-bis(diphenylphosphino)ferrocene]palladium[II] chloride, tris(dibenzylideneacetone)dipalladium[0], bis(benzonitrile)dichloropalladium[II], dichlorobis(triphenylphosphine)palladium[II] and [1,3-bis(diphenylphosphino)propane]nickel[II] chloride. Preferred bases include alkali metal carbonates, alkali metal phosphates, thallium carbonate and silver oxide. A preferred additive is lithium chloride or potassium bromide. Preferred solvents and temperatures are dioxane, THF, diethyl ether, benzene, dimethylformamide (DMF) and N-methyl-2-pyrrolidinone (NMP) or mixtures thereof from about $20°$ C. to about the boiling point of the solvent or $150°$ C., whichever is lower.

In some cases the compound of formula IV is partly or completely reduced by the organometallic reagent to produce the pyrimidinone of formula V wherein $R^6$ is a hydrogen atom.

In a more preferred embodiment, the process of the present invention is used to produce pyrimidinones of formula V wherein Ar is 2-furyl, 3-furyl, 4-chloro-2-furyl, 5-chloro-2-furyl, 5-chloro-3-furyl, 2,5-dichloro-3-furyl, 2-naphthyl, phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 2-fluorophenyl, 2-chlorophenyl, 2-trifluoromethoxyplhenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 2-pyridyl, 4-chloro-2-pyridyl, 6-chloro-2-pyridyl, 4,6-dichloro-2-pyridyl, 3-pyridyl, 5-bromo-3-pyridyl, 5,6-dichloro-3-pyridyl, 5-chloro-3-pyridyl, 5-fluoro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl, 2,6-dichloro-4-pyridyl, 2-thienyl, 3-thienyl, 4-chloro-2-thienyl, 5-chloro-2-thienyl, 5-chloro-3-thienyl, 2,5-dichloro-3-thienyl or 3,4-methylenedioxyphenyl;

$R^3$ is ethyl, allyl, 3-chloroallyl, prop-2-ynyl, but-2-ynyl, pent-2-ynyl or 2-methoxyethyl;

$R^5$ is methyl, ethyl, methoxy, methylthio, difluoromethoxy or trifluoromethoxy; and $R^6$ is methyl, ethyl, n-propyl, n-butyl, n-pentyl, n-hexyl, sec-butyl, isopropyl, isobutyl, vinyl, isopropenyl, allyl, ethynyl, prop-1-ynyl, 1-methylprop-2-ynyl, prop-2-ynyl, trifluoromethyl, pentafluoroethyl, trichloromethyl, bromomethyl, chloromethyl, difluoromethyl, chlorodifluoromethyl, phenyl or 3-thienyl.

In another embodiment of this invention, when $R^6$ is a 1-alkynyl group, the alkyne $R^6H$ may be used in place of $R^6M$ in the presence of a catalyst and in the presence of a base from about 20° C. to about 150° C. in a solvent in process step (iii). A preferred alkyne $R^6H$ is (trimethylsilyl) acetylene, a preferred catalyst is dichlorobis (triphenylphosphine)palladium[II], a preferred base is triethylamine and a preferred solvent is DMF.

In yet another embodiment of this invention, when $R^3$ in a compound of formula IV is a terminal alkynyl group, for example, $R^3$ is $(CH_2)_nC\equiv CH$ wherein n is 1, 2, 3 or 4, the alkyne can be protected as a silyl derivative in an intermediate step (iia) by deprotonation with a base and reaction with a silylating agent $R^aR^bR^cSiY'$ wherein $R^a$, $R^b$ and $R^c$ are independently selected from $(C_1-C_6)$alkyl and phenyl and Y' is a good leaving group, prior to coupling with the organometallic reagent $R^6M$ in process step (iii). Preferred bases include alkyllithiums, alkyl magnesiumhalides and alkali metal amides. Preferred silylating agents $R^aR^bR^cSiY'$ are silyl chlorides and triflates wherein Y' is chloro or trifluoromethanesulfonyloxy. The coupling product of formula V, wherein $R^3$ is $(CH_2)_nC\equiv CSiR^aR^bR^c$, may be deprotected to give a compound of formula V wherein $R^3$ is $(CH_2)_nC\equiv CH$ if desired.

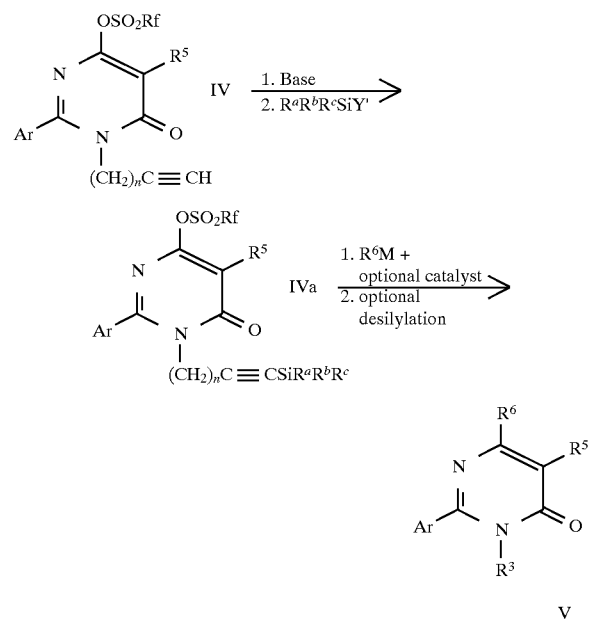

The substituent preferences for Ar, $R^5$ and Rf in the compound of formula IVa are the same as those described hereinabove for the compound of formula IV.

In still another embodiment of this invention are compounds of formula III which are useful as intermediates in the process of the present invention to the herbicidal compounds of formula V wherein Ar and $R^5$ are the same as those described hereinabove for the compound of formula III in the process embodiment of the present invention and $R^3$ is a $(C_4-C_6)$alkyl, $(C_3-C_6)$alkenyl, $(C_3-C_6)$alkynyl, $(C_1-C_6)$alkoxy$(C_2-C_6)$alkyl, or silyl$(C_3-C_6)$alkynyl of the form $(CH_2)_nC\equiv CSiR^aR^bR^c$ wherein n is 1, 2,3 or 4 and $R^a$, $R^b$, and $R^c$ are independently selected from $(C_1-C_6)$alkyl and phenyl; or is a $(C_4-C_6)$alkyl, $(C_3-C_6)$alkenyl, $(C_3-C_6)$alkynyl, $(C_1-C_6)$alkoxy$(C_2-C_6)$alkyl, or silyl$(C_3-C_6)$alkynyl of the form $(CH_2)_nC\equiv CSiR^aR^bR^c$ wherein n is 1, 2, 3 or 4 and $R^a$, $R^b$, and $R^c$ are independently selected from $(C_1-C6)$alkyl and phenyl wherein each of the foregoing groups is substituted with up to five halogen atoms.

In yet still another embodiment of this invention are compounds of formula IV which are useful as intermediates in the process of the present invention to the herbicidal compounds of formula V wherein Ar, $R^3$, $R^5$ and Rf are the same as those described hereinabove for the compound of formula IV in the process embodiment of the present invention.

The following examples serve only to illustrate the utilization of the present invention and are not meant to limit the scope of the present invention which is defined by the claims.

A. EXAMPLES OF CONVERSION OF I AND II TO III

Example 1

Preparation of 2-(2,6-dichloro-4-pyridyl)-5-ethyl-6-hydroxy-3-propargyl-4(3H)-pyrimidinone To a cold (−78° C.) solution of 2,6-dichloropyridine-4-(N-propargyl)carboxamidine (0.228 g, 1.0 mmol) in 5 mL of THF was added sodium bis(trimethylsilyl)amide (1.0 mL, 1 mmol, 1 equiv, 1M solution in THF). The reaction mixture was stirred for 10 min at −78° C. and a cold (−78° C.)

solution of ethylmalonyl dichloride (0.186 g, 1.1 mmol, 1.1 equiv) in 5 mL of THF was added via a canula over 10 min. The reaction mixture was stirred for 40 min, quenched with 10 mL of water and warmed to room temperature. After diluting with 30 mL of ethyl acetate, the organic layer was successively washed with water (10 mL), saturated sodium chloride (10 mL), dried (MgSO$_4$) and concentrated to give a yellow solid. The crude product was purified by flash chromatography (silica gel, CH$_2$Cl$_2$/MeOH, 98/2) to afford 0.205 g (63%) of 2-(2,6-dichloro-4-pyridyl)-5-ethyl-6-hydroxy-3-propargyl-4(3H)-pyrimidinone: mp 200°–202° C.; IR (KBr) 3237, 3170, 1623, 1541, 1528, 1361 cm$^{-1}$; $^1$H NMR (270 MHz, CDCl$_3$) δ 1.11 (t, J=7.6 Hz, 3H), 2.44–2.54 (m, 3H), 4.59 (d, J=2.3 Hz, 2H), 7.59 (s, 2H), 9.25 (br s, 1H); Anal. Calcd for C$_{14}$H$_{11}$Cl$_2$N$_3$O$_2$: C, 51.87;H, 3.42;N, 12.96. Found: C, 51.67;H, 3.59;N, 12.70.

Example 2
Preparation of 2-(2.6-dichloro-4-pyridyl)-6-hydroxy-5-(1-methylethyl)-3-propargyl-4(3H)-pyrimidinone A stirred solution of 10.32 g (45.3 mmol) of 2,6-dichloropyridine-4-(N-propargyl)carboxamidine in 250 mL of dry THF was cooled to –70° C. and 50 mL of 1.0M (50.0 mmol) sodium bis(trimethylsilyl)amide in THF was added over 10 min. The mixture was stirred at –70° C. for 40 min and a solution of 8.47 g (46.3 mmol) of isopropylmalonyl dichloride in 50 mL of THF was added dropwise over 40 min. The mixture was stirred at –70° C. for 40 min and quenched by addition of 50 mL of water. The mixture was removed from the cooling bath and the bulk of the THF was evaporated under reduced pressure. The residue was diluted with 150 mL of 5% aqueous hydrochloric acid and extracted with two 200 mL portions of ethyl acetate. The combined organic layers were washed with 50 mL of brine and dried over MgSO$_4$. Removal of the solvent under reduced pressure afforded 15.65 g of crude 2-(2,6-dichloro-4-pyridyl)-6-hydroxy-5-(1-methylethyl)-3-propargyl-4(3H)-pyrimidinone-as a viscous oil. $^1$H NMR (CDCl$_3$) δ 1.25 (d, 6H), 2.45 (t, 1H), 3.3 (m, 1H), 4.55 (d, 2H), 7.6 (s, 2H). This material was used without further purification.

Example 3
Preparation of 2-(2.6-dichloro-4-pyridyl)-6-hydroxy-5-methoxy-3-propargyl-4(3H)-pyrimidinone A stirred solution of 52.44 g (0.23 mol) of 2,6-dichloropyridine-4-(N-propargyl)carboxamidine in 600 mL of dry THF, under a nitrogen atmosphere, was cooled to –70° C. and 242.6 mL (0.24 mol) of 1.0M sodium bis(trimethylsilyl)amide in THF was added dropwise over 1.25 hours, maintaining the temperature at or below –70° C. The reaction mixture was stirred an additional 15 minutes at –70° C. and a solution of 40 g (0.23 mol) of methoxymalonyl dichloride in 100 mL of dry THF was added dropwise over 1.5 hours. The mixture was stirred at –70° C. for 30 minutes and quenched by the addition of 125 mL of water. The bulk of the THF was removed on the rotovap and the residue was taken up in ethyl acetate and 3M HCl. The layers were separated and the aqueous layer was extracted four times with ethyl acetate. The organic layers were combined and washed once with 3M HCl, once with brine, dried over MgSO$_4$ and concentrated to yield 57 g of a golden solid. The product was purified by trituration with a minimal amount of CH$_2$Cl$_2$ to yield 5.8g (7.7%) of 2-(2,6-dichloro-4-pyridyl)-6-hydroxy-5-methoxy-3-propargyl-4(3H)-pyrimidinone, as an off white solid. Mp=227°–228.5° C. $^1$H NMR (d$_6$ DMSO) δ 3.48 (t, 1H), 3.75 (s, 3H), 4.61 (d, 2H) 7.92 (s, 2H), 11.8 (s, 1H).

B. EXAMPLES OF PREPARATION OF IV

Example 4
Preparation of 2-(2.6-dichloro-4-pyridyl)-5-ethyl-3-propargyl-6-trifluoromethanesulfonyloxy-4(3H)-pyrimidinone To a stirred, cold (–78° C.) solution of 2-(2,6-dichloro-4-pyridyl)-5-ethyl-6-hydroxy-3-propargyl-4(3H)-pyrimidinone (0.10 g, 0.309 mmol) in 5 mL of dichloromethane was added collidine (0.06 mL, 0.455 mmol, 1.47 equiv). The reaction mixture was stirred for 5 min and trifluoromethanesulfonic anhydride (0.07 mL, 0.417 mmol; 1.35 equiv) was added. The reaction mixture was stirred for 30 min at –78° C., quenched with 5 mL of water and diluted with 30 mL of CH$_2$Cl$_2$. The organic layer was separated, washed with 15 mL of saturated sodium chloride, dried (MgSO$_4$), filtered and concentrated to give a light brown oil. The crude product was purified by preparative TLC (ethyl acetate/hexane: 2/8) to produce 0.105 g (74%) of 2-(2,6-dichloro-4-pyridyl)-5-ethyl-3-propargyl-6-trifluoromethanesulfonyloxy-4(3H)-pyrimidinone as a white solid: mp 112°–114° C.; IR (KBr) 3236, 2125, 1692, 1620, 1555, 1423, 1293, 1201 cm$^{-1}$; $^1$H NMR (270 MHz, CDCl$_3$) δ 1.24 (t, J=7.6 Hz, 3H), 2.56 (t, J=2.3 Hz, 1H), 2.66 (q, J=14.8 Hz, 2H), 4.63 (d, J=2.3 Hz, 2H), 7.66 (s, 2H); Anal. Calcd for C$_{15}$H$_{10}$Cl$_2$F$_3$N$_3$O$_4$S: C, 39.49;H, 2.21;N, 9.21. Found: C, 39.69;H, 2.42;N, 9.28.

Example 5
Preparation of 2-(2,6-dichloro-4-pyridyl)-5-(1-methylethyl)-3-propargyl-6-trifluoromethanesulfonyloxy-4(3H)-pyrimidinone A stirred solution of 15.65 g of crude 2-(2,6-dichloro-4-pyridyl)-6-hydroxy-5-(1-methylethyl)-3-propargyl-4(3H)-pyrimidinone and 9 mL (77.3 mmol) of 2,6-lutidine in 100 mL of dichloromethane was cooled to –70° C. and 12 mL (71.3 mmol) of trifluoromethanesulfonic anhydride was added over 2 min. The cooling bath was allowed to expire and the mixture was stirred overnight at room temperature. The mixture was evaporated under reduced pressure to remove dichloromethane. The residue was taken up in 400 mL of ether and washed with two 100 mL portions of cold 5% aqueous hydrochloric acid and two 100 mL portions of cold 5% aqueous NaOH, and dried over MgSO$_4$. Removal of the solvent under reduced pressure afforded 12.64 g of a dark oil. This material was purified by flash chromatography on a column of 100 g of silica gel which was eluted successively with 250 mL portions of 0, 10, 20, 30, 40 and 60% ether in hexanes. Fractions of 250 mL were collected. Fractions 5 through 9 were combined and concentrated under reduced pressure to afford 10.34 g (48%) of 2-(2,6-dichloro-4-pyridyl)-5-(1-methylethyl)-3-propargyl-6-trifluoromethanesulfonyloxy-4(3H)-pyrimidinone as a syrup. $^1$H NMR (CDCl$_3$) δ 1.35 (d, 6H), 2.55 (t, 1H), 3.3 (m, 1H), 4.6 (d, 2H), 7.7 (s, 2H).

Example 6
Preparation of 2-(2.6-dichloro-4-pyridyl)-5-methoxy-3-propargyl-6-trifluoromethanesulfonyloxy-4(3H)-pyrimidinone A stirred solution of 5.05g (0.015 mol) of 2-(2,6-dichloropyridyl)-6-hydroxy-5-methoxy-3-propargyl-4(3H)-pyrimidinone and 2.9 mL (0.025 mol) of 2,6-lutidine in 100 mL of dichloromethane was cooled to –70° C. and 3.9 mL (0.023 mol) of trifluoromethanesulfonic anhydride was added dropwise over 30 minutes. The mixture was stirred at –70° C. for 30 minutes and allowed to warm to room temperature. After 1.5 hours, the mixture was quenched by the addition of 50 mL of water. The organic layer was separated and rotovapped to remove the dichloromethane. The residue was taken up in ethyl acetate and added back to the water layer. 3M HCl was added and the layers were separated. The organic layer was washed twice more with 3M HCl. The aqueous layers were combined and back extracted once with ethyl acetate. The ethyl acetate layers were combined and washed 3 times with saturated NaHCO$_3$, dried over MgSO$_4$ and concentrated to yield 7.10 g of product, as a dark brown solid. The product was triturated with dichloromethine and ether to yield a sand colored solid, which was then dissolved in ether and dichloromethane and passed through a four inch plug of silica gel. The filtrate was concentrated to yield 4.15g of 2-(2,6-dichloropyridyl)-5-methoxy-3-propargyl-6-trifluoromethanesulfonyloxy 4(3H) -pyrimidinone, as a white solid, m.p. =133°–135° C. The filtrate from the trituration was passed through a plug of silica gel, using ether and dichloromethane, and concentrated to yield 2.5 g more of the product as a light brown solid. $^1$H NMR (CDCl$_3$) δ 2.6(1H,t), 4.2(3H,s), 4.62(2H,d), 7.65(2H,s).

Example 7
Telescoped Preparation of 5-ethyl-2-phenyl-3-propargyl-6-trifluoromethanesulfonyloxy-4(3H)-pyrimidinone from N-propargylbenzamidine and ethylmalonyl dichloride To a cold (–78° C.) solution of N-propargylbenzamidine (5.50 g, 34.77 mmol) in 150 mL of THF was added sodium bis(trimethylsilyl)amide (36.51 mL, 36.51 mmol, 1.05 equiv, 1M solution in THF) over 20 minutes. The reaction mixture was stirred for 5 minutes at –78° C., followed by the addidion of a cold (–78° C.) solution of ethylmalonyl dichloride (6.46 g, 38.25 mmol, 1.1 equiv.) in 150 mL of THF via a canula over 2 hours. After stirring for 30 minutes, the reaction mixture was quenched with 100 mL of water, warmed to room temperature, and diluted with 300 mL of ethyl acetate and 100 mL of water. The organic layer was successively washed with 200 mL of water and 200 mL of saturated sodium chloride, dried (MgSO$_4$), filtered, and concentrated to give a solid. The crude mixture was azeotropically evaporated with 200 mL of toluene to remove residual hexamethyldisilazane, affording 8.28 g of 5-ethyl-6-hydroxy-2-phenyl-3-propargyl-4(3H)-pyrimidinone which was used without further purification.

To a cold (–78° C.) suspension of 6.5 g (25.56 mmol) of the above 2-phenyl-5-ethyl-6-hydroxy-3-propargyl-4(3H)-pyrimidinone in 150 mL of CH$_2$Cl$_2$ was added collidine (5.06 mL, 38.34 mmol, 1.5 equiv) via a syringe. The reaction mixture was stirred for 15 minutes, followed by the addition of trifluoromethanesulfonic anhydride (6.44 mL, 38.34 mmol, 1.5 equiv). After stirring for 15 minutes, the reaction mixture-was quenched with 100 mL of water, diluted with 250 mL of CH$_2$Cl$_2$, and warmed to room temperature. The organic layer was separated, and the aqueous layer was extracted with 100 mL of CH$_2$Cl$_2$. The combined organic extracts were successively washed with 2×100 mL of water, 2×100 mL of saturated sodium chloride, dried (MgSO$_4$), filtered, and concentrated. The crude product was purified by flash chromatography (silica gel, ethyl acetate/hexane, 2/8) to afford 4.2 g (42%, based on N-propargylbenzamidine) of 5-ethyl-2-phenyl-3-propargyl-6-trifluoromethanesulfonyloxy-4(3H)-pyrimidinone: mp 159°–160° C.; IR (KBr)3281, 2992, 2936, 2133, 1710, 1675, 1520, 1421, 1196 cm$^{-1}$; $^1$H NMR (270 MHz, CDCl$_3$) δ 1.24 (t, J=7.3 Hz, 3Ht), 2.46 (t,j=2.3 Hz, 1H), 2.65 (q, J=14.8 Hz, 2H), 4.64 (d,J=2.3 Hz, 2H), 7.55–7.80 (m, 5H): $^{13}$C NMR (68 MHz, CDCl3) δ 12.2, 17.8, 37.8, 73.9, 77.6, 116.2, 120.1, 128.7, 129.0, 131.7, 132.6, 156.7, 158.0, 163.0. Anal. Calcd for C$_{16}$H$_{13}$F$_3$N$_2$O$_4$S: C, 49.74;H, 3.39;N, 7.25. Found: C, 50.02;H, 3.56;N, 7.18.

Example 8
Preparation of 5-ethyl-2-phenyl-6-trifluoromethanesulfonyloxy-3-(3-trimethylsilyl)propargyl-4(3H)-pyrimidinone To a stirred, cold (–78° C.) solution of 5-ethyl-2-phenyl-3-propargyl-6-trifluoromethanesulfonyloxy-4(3H)-pyrimidinone (3.0 g, 7.77 mmol) in 75 mL of THF was added n-butyllithium (3.4 mL, 8.54 mmol, 1.1 equiv, 2.5M in hexane) dropwise. After stirring for 5 minutes, trimethylsilyl chloride (1.1 mL, 8.54 mmol, 1.1 equiv) was added, and the stirring was continued for 30 minutes at –78° C. and 1 hour at room temperature. The reaction mixture was quenched with 50 mL of water and diluted with 50 mL of ethyl acetate. The two layers were separated and the aqueous layer was extracted with 50 mL of ethyl acetate. The combined organic layers were washed with 2×50 mL of saturated sodium chloride, dried (MgSO$_4$), filtered, and concentrated. The crude product was purified by flash chromatography (silica gel, ethyl acetate/hexane, 1/9) to afford 2.03 g (56%) of 5-ethyl-2-phenyl-6-trifluoromethanesulfonyloxy-3-(3-trimethylsilyl)propargyl-4(3H)-pyrimidinone: mp 119°–120° C.; IR (KBr) 2978, 2181, 1677, 1620, 1518, 1416, 1218, 1200 cm$^{-1}$; $^1$H NMR (270 MHz, CDCl$_3$) δ 0.20 (s, 9H) 1.23 (t, J=7.3 Hz, 3H), 2.64 (q, J=14.8 Hz, 2H), 4.66 (s, 2H), 7.50–7.80 (m, 5H); $^{13}$C NMR (68 MHz, CDCl$_3$) δ-0.2, 12.2, 17.9, 38.4, 91.0, 99.0, 116.1, 121.0, 128.7, 128.8, 131.5, 132.8, 156.7, 158.2, 162.9. Anal. Calcd for C$_{19}$H$_{21}$F$_3$N$_2$O$_4$SSi:. C, 49.77;H, 4.62;N, 611. Found C, 49.42;H, 4.34;N, 6.00.

C. EXAMPLES OF CONVERSION OF IV TO V

Example 9
Preparation of 2-(2,6-dichloro-4-pyridyl)-5-ethyl-6-methyl-3-propargyl-4(3H)-pyrimidinone To a stirred, cold (–78° C.) solution of CuCN (1.91 g, 20 mmol) in 100 mL of THE was added methyllithium (30 mL, 42 mmol, 2.1 equiv, 1.4M in diethyl ether) over 10 min. After stirring for 15 min, this solution was added over 10 min via a canula to a cold (–78° C.) solution of 2-(2,6-dichloro-4-pyridyl)-5-ethyl-3-propargyl-6-trifluoromethanesulfonyloxy-4(3H)-pyrimidinone in 20 mL of THF. The reaction mixture was stirred for 30 min, quenched with 15 mL of 10% concentrated NH$_4$OH/saturated NH$_4$Cl, diluted with 200 mL of ethyl acetate and warmed to room temperature. The organic layer was separated and the aqueous layer was extracted with ethyl acetate (2×100 mL). The combined organic layers were dried (MgSO$_4$), filtered and concentrated to give a semi oil. The crude product was purified by flash chromatography (silica gel, ethyl acetate/hexane, 2/8) to afford 2.29 g (71%) of 2-(2,6-dichloro-4-pyridyl)-5-ethyl-6-methyl-3-propargyl-4 (3H)-pyrimidinone as a white solid: mp 143°–144° C.; IR (KBr) 3220, 2125, 1668, 1584, 1541, 1515, 1367 cm$^{-1}$; $^1$H NMR (270 MHz, CDCl$_3$) δ 1.16 (t, J=7.6 Hz, 3H), 2.35 (s, 3H), 2.43 (t, J=2.6 Hz, 1H), 2.62 (q, J=14.8 Hz, 2H), 4.56 (d, J=2.6 Hz, 2H), 7.60 (s, 2H).

Example 10
Preparation of 2-(2.6-dichloro-4-pyridyl)-5-(1-methylethyl) -3-propargyl-4(3H)-pyrimidinone A stirred suspension of 0.65 g (7.3 mmol) of copper(I) cyanide in 20 mL of dry THF was cooled to –70° C. and a mixture of 18 mL of 0.85M ethyllithium in benzene (15.3 mmol) and 20 mL of ether was added by canula over 5 min. The temperature of the mixture rose to –50° C. The cooling bath was removed and the mixture was allowed to warm to –40° C., then recooled to –70° C. A solution of 1.70 g (3.6 mmol) of 2-(2,6-dichloro-4-pyridyl)-5-(1-methylethyl)-3-propargyl-6-trifluoromethanesulfonyloxy-4(3H)-pyrimidinone in 12 mL of THF was added rapidly. The resulting black mixture was allowed to stir at –70° C. for 40 min and poured into 100 mL of 9:1 saturated aqueous NH₄Cl: concentrated NH₄OH. The mixture was extracted with two 100 mL portions of ether. The combined ether extracts were washed with 50 mL of concentrated NH₄OH and dried over MgSO₄. Removal of the solvent under reduced pressure afforded 1.66 g of an oil. This material was purified by flash chromatography on a column of 30 g of silica gel which was eluted successively with 100 mL portions of 0, 10, 20, 30, 40, 50, 60 and 70% ether in hexanes. Fractions of 25 mL were collected. Fractions 16 through 18 were combined and concentrated under reduced pressure to afford 0.42 g of 2-(2,6-dichloro-4-pyridyl)-5-(1-methylethyl)-3-propargyl-4(3H)-pyrimidinone as a syrup. $^1$H NMR (CDCl₃) δ 1.35 (d, 6H), 2.5 (t, 1H), 3.15 (m, 1H), 4.6 (d, 2H), 7.6 (s, 2H), 7.8 (s, 1H).

Example 11
Preparation of 2-(2.6-dichloro-4-pyridyl)-5,6-diethyl-3-propargyl-4(3H)-pyrimidinone To a stirred solution of 0.46 g (1.0 mmol) of 2-(2,6-dichloro-4-pyridyl)-5-ethyl-3-propargyl-6-trifluoromethanesulfonyloxy-4(3H)-pyrimidinone, 0.06 g (0.07 mmol) of dichloro[1,1-bis(diphenylphosphino)ferrocene]palladium(II) dichloromethane complex and 0.43 g (2.0 mmol) of K₃PO₄ in 5 mL of DMF was added 1.1 mL of 1.0M triethylborane in THF (1.1 mmol). The mixture was stirred at room temperature for 22 h and treated with 1 mL of 1:1 12.5% aqueous NaOH:30% H₂O₂. Gas evolution occurred. The mixture was diluted with 150 mL of ethyl acetate, washed with 50 mL of water and 50 mL of brine, and dried over MgSO₄. Removal of the solvent under reduced pressure afforded 0.55 g of a dark oil. This material was purified by flash chromatography on a column of 20 g of silica gel which was eluted with 50 mL portions of 0, 20, 40, 60, 80 and 100% ether in hexanes. Fractions of 15 mL were collected. Fractions 8–10 were combined and concentrated to afford 0.05 g of a white solid. Comparison of the $^1$H NMR and mass spectra of this material with those of an authentic sample demonstrated the presence of 2-(2,6-dichloro-4-pyridyl)-5,6-diethyl-3-propargyl-4(3H)-pyrimidinone.

Example 12
Preparation of 2-(2.6-dichloro-4-pyridyl)-5-methoxy-6-methyl-3-=propargyl-4(3H)-pyrimidinone A stirred suspension of 0.126 g (1.41 mmol) of copper(I) cyanide in 6 mL of dry THF, under a nitrogen atmosphere, was cooled to −70° C. and 2.1 mL (2.94 mmol) of 1.4M methyllithium in ether was added dropwise over 1h. The mixture was stirred at −70° C. for 15 minutes, allowed to warm to −50° C. and recooled to −70° C. The cuprate solution was added via a canula under nitrogen pressure to a stirred solution of 300 mg (0.65 mmol) of 2-(2,6-dichloro-4-pyridyl)-5-methoxy-3-propargyl-6-trifluoromethanesulfonyloxy-4(3H)-pyrimidinone in 5 mL of dry THF at −70° C. The reaction mixture was stirred for 0.5h at −70° C. and quenched by pouring into a solution of 20 mL of 9:1 saturated aqueous NH₄Cl: concentrated aqueous NH₄OH. The organic layer was separated and the THF was removed in vacuo. Ethyl acetate was added to the residue and the solution was combined with the aqueous layer. NH₄OH was added to the mixture and the layers were separated. The organic layer was washed once with NH₄OH. The aqueous layers were combined and washed once with ethyl acetate. The organic layers were combined, dried over MgSO₄ and concentrated to yield 0.17 g of oily product containing approximately a 3:2 mixture of 2-(2,6-dichloro-4-pyridyl)-5-methoxy-6-methyl-3-propargyl-4(3H)-pyrimidinone and 2-(2,6-dichloro-4-pyridyl)-5-methoxy-3-propargyl-4(3H)-pyrimidinone. The former compound gave $^1$H NMR (CDCl₃) δ 2.35 (s, 3H), 2.52 (t, 1H), 3.9 (s, 3H), 4.65 (d, 2H), 7.64 (s, 2H).

Example 13
Preparation of 5-ethyl-2-phenyl-3-(3-trimethylsilyl)propargyl-6-vinyl-4(3H)-pyrimidinone To a stirred mixture of 5-ethyl-2-phenyl-6-trifluoromethanesulfonyloxy-3-(3-trimethylsilyl)propargyl-4(3H)-pyrimidinone (0.800 g, 1.744 mmol), tetrakis(triphenylphosphine)palladium(0) (0.040 g, 0.032 mmol, 0.02 equiv) and lithium chloride (0.222 g, 5.232 mmol, 3 equiv) in 12 mL of dioxane was added vinyltributyltin (0.71 mL, 2.442 mmol, 1.4 equiv) at room temperature. The reaction mixture was then heated up to ~110° C. and stirred for 30 minutes. The mixture was cooled to room temperature and diluted with 20 mL of water and 50 mL of ethyl acetate. The organic layer was separated, and the aqueous layer was extracted with 30 mL of ethyl acetate. The combined organic extracts were washed with 30 mL of saturated sodium chloride, dried (MgSO₄), filtered, and concentrated. The crude product was purified by flash chromatography (silica gel, ethyl acetate/hexane, 1/9) to afford 0.48 g (82%) of 5-ethyl-2-phenyl-3-(3-trimethylsilyl)propargyl-6-vinyl-4(3H)-pyrimidinone: mp 91°–3° C.: IR (KBr) 2964, 2168, 1661, 1563, 1520, 1400, 1246, 1027 cm$^{-1}$ $^1$H NMR (270 MHz, CDCl3) δ 0.17 (s, 9H) 1.19 (t,J=7.3 Hz, 3H), 2.73 (q, J=14.8 Hz, 2H), 4.62 (s, 2H), 5.61 (dd, J₁=2.0 Hz, J₂=2=10.6 Hz, 1H), 6.48 (dd, J₁=2.0 Hz, J₂=16.8 Hz, 1H), 6.91 (dd, J₁=10.6 Hz, J₂=16.8 Hz, 1H), 7.48–7.74 (m, 5H), $^{13}$C NMR (68 MHz, CDCl3) δ-0.2, 13.5, 18.6, 37.2, 89.4, 100.2, 123.2, 128.4, 128.5, 130.2, 131.2, 134.9, 152.2, 156.3, 162.5.

Example 14
Preparation of 5-ethyl-2-phenyl-3-propargyl-6-vinyl-4(3H)-pyrimidinone To a stirred solution of 5-ethyl-2-phenyl-3-(3-trimethylsilyl)propargyl-6-vinyl-4(3H)-pyrimidinone (0.35 g, 1.04 mmol) in 10 mL of MeOH was added 1mL of acetic acid followed by potassium fluoride (0.302 g, 5.20 mmol, 5 equiv) at room temperature. The reaction mixture was stirred for 4.5 hours. The solvent was removed, and the residue was dissolved in 50 mL of ethyl acetate and 20 mL of water. The organic layer was separated, and the aqueous layer was extracted with 30 mL of ethyl acetate. The combined organic extracts were washed with 30 mL of saturated sodium chloride, dried (MgSO₄) filtered, and concentrated. The crude product was purified by flash chromatography (silica gel, ethyl acetate/hexane, 1/9) to afford 0.254 g (92%) of 5-ethyl-2-phenyl-3-propargyl-6-vinyl-4(3H)-pyrimidinone: mp 113°–5° C.; IR (KBr) 3189, 2959, 2105, 1645, 1562, 1530, 1409, 1180 cm$^{-1}$; $^1$H NMR (270 MHz, CDCl3) δ 1.01 (t, J=7.3 Hz, 3H), 2.16 (t, J=1.3 Hz, 1H), 2.37 (q, J=14.8 Hz, 2H), 4.41 (d, J=1.3 Hz, 2H), 5.44 (dd, J₁=2.0 Hz, J₂=10.5 Hz, 1H), 6.30(dd, J₁=2.0 Hz, J₂=16.8 Hz, 1H), 6.73 (dd, J₁=10.5 Hz, J₂=16.8 Hz, 1H), 7.33–7.57 (m, 5H); $^{13}$C NMR (68 MHz, CDCl₃) δ 13.5, 18.6, 36.8, 72.8, 78.6, 123.4, 124.2, 128.5, 128.8, 130.5, 131.2, 134.8, 152.4, 156.2, 162.7.

Example 15
Preparation of 5-ethyl-2-phenyl-6-(2-trimethylsilyl)ethynyl-3-(3-trimethylsilyl)propargyl-4(3H)-pyrimidinone To a stirred mixture of 5-ethyl-2-phenyl-6-trifluoromethanesulfonyloxy-3-(3-trimethylsily)propargyl-4(3H)-pyrimidinone (0.800 g, 1.744 mmol), bis(triphenylphosphine)palladium(ll) chloride (0.024 g, 0.032 mmol, 0.02 equiv) and triethylamine (0.48 mL, 3.488 mmol, 2 equiv) in 16 mL of DMF was added (trimethylsilyl)

acetylene (0.4 mL, 2.616 mmol, 1.5 equiv) at room temperature. The reaction mixture was then heated up to ~65° C and stirred for 3 hours. The mixture was cooled to room temperature and the solvent was removed under vacuum. The residue was dissolved in 50 mL of ethyl acetate and 20 mL of water. The organic layer was separated, and the aqueous layer was extracted with 30 mL of ethyl acetate. The combined organic extracts were successively washed with 2×30 mL of water, 30 mL of saturated sodium chloride, dried (MgSO$_4$), filtered, and concentrated. The crude product was purified by flash chromatography (silica gel, ethyl acetate/hexane, 1/9) to afford 0.67 g (95%) of compound 5-ethyl-2-phenyl-6-(2-trimethylsilyl)ethynyl-3-(3-trimethylsilyl)propargyl-4(3H)-pyrimidinone: mp 97°–8° C.; IR (KBr) 2958, 2177, 1669, 1530, 1409, 1240 cm$^{-1}$; $^1$H NMR (270 MHz, CDCl$_3$) δ 0.15 (s, 9H), 0.25 (s, 9H), 1.23 (t, J=7.6 Hz, 3H), 2.78 (q, J=14.8 Hz, 2H), 4.59 (s, 2H), 7.46–7.66 (m, 5H); $^{13}$C NMR (68 MHz, CDCl$_3$) δ-0.4, -0.3, 12.2, 21.5, 37.1, 89.8, 99.6, 100.5, 103.2, 128.2, 128.6, 130.4, 131.7, 134.2, 141.7, 157.9, 161.0. Anal. Calcd for $C_{23}H_{30}N_2OSi_2$: C, 67.93;H, 7.44;N, 6.89. Found: C, 68.10: H, 7.34;N, 9.93.

Example 16

Preparation of 5-ethyl-6-ethynyl-2-phenyl-3-propargyl-4(3H)-pyrimidinone

To a stirred solution of 5-ethyl-2-phenyl-6-(2-trimethylsilyl)ethynyl-3-(3-trimethylsilyl)propargyl-4(3H)-pyrimidinone (0.400 g, 0.984 mmol) in 10 mL of MeOH was added 1 mL of acetic acid followed by potassium fluoride (0.572 g, 9.836 mmol, 10 equiv) at room temperature. The reaction mixture was stirred for 3 hours. The solvent was removed, and the residue was dissolved in 50 mL of ethyl acetate and 20 mL of water. The organic layer was separated, and the aqueous layer was extracted with 30 mL of ethyl acetate. The combined organic extracts were washed with 30 mL of saturated sodium chloride, dried (MgSO$_4$), filtered, and concentrated, The crude product was purified by flash chromatography (silica gel, ethyl acetate/hexane, 2/8) to afford 0.249 g (97%) of 5-ethyl-6-ethynyl-2-phenyl-3-propargyl-4(3H)-pyrimidinone: mp 134°–6° C.; IR (KBr) 3254, 3237, 2964, 2105, 1669, 1566,1524,1409,1179 cm$^{-1}$; $^1$H NMR (270 MHz, CDCl$_3$) δ 1.06 (t, J=7.3 Hz, 3H), 2.17 (t, J=2.3 Hz, 1H), 2.61 (q, J=14.8 Hz, 2H), 3.29 (s, 1H), 4.40 (d, J=2.3 Hz, 2H), 7.29–7.51 (m, 5H); $^{13}$C NMR (68 MHz, CDCl$_3$) δ 12.5,21.3,36.8,73.1, 78.0,79.7,84.6,128.2, 128.8, 130.6, 132.1, 133.8, 141.2, 157.9, 161.2.

We claim:

1. A process for making the pyrimidinone compound of formula V

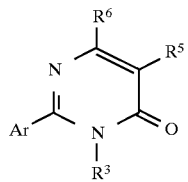

which comprises the steps of (i) reacting an N-substituted amidine of formula I with an activated malonic acid derivative of formula II at room temperature or below in the presence of a base and a solvent or solvent mixture to form a hydroxypyrimidinone compound of formula III

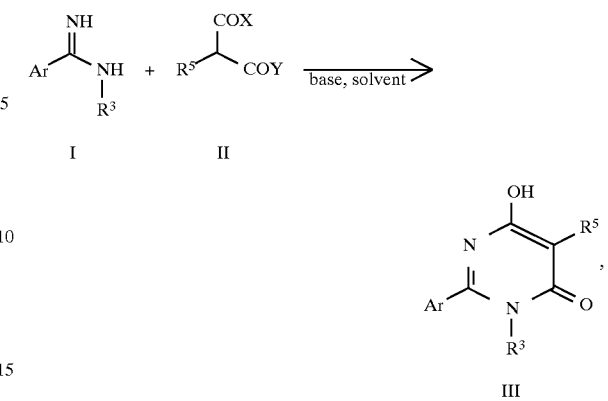

(ii) reacting the resulting hydroxypyrimidinone compound of formula III with a compound of the formula RfSO$_2$Z to form a sulfonyloxypyrimidinone compound of formula IV

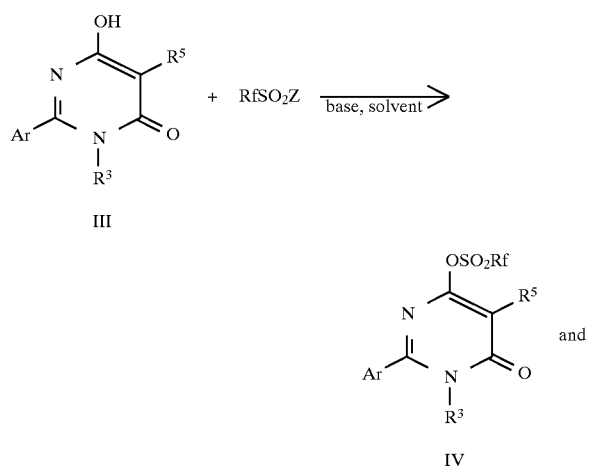

(iii) reacting the resulting sulfonyloxypyrimidinone compound of formula IV with an organometallic reagent of the formula R$^6$M, in the presence or absence of catalysts, a base and other additives, at a temperature from about −80° C. to about 150° C. in a solvent or mixture of solvents to form a pyrimidinone compound of formula V wherein Ar is a (C$_6$–C$_{10}$)aryl or (C$_4$–C$_5$)heteroaromatic group, or a (C$_6$–C$_{10}$)aryl or (C$_4$–C$_5$)heteroaromatic group substituted with up to three substituents independently selected from bromo, chloro, fluoro, (C$_1$–C$_{12}$) alkyl, cyclo(C$_3$–C$_8$)alkyl, (C$_2$–C$_{12}$)alkenyl, cyclo (C$_3$–C$_8$)alkenyl, (C$_2$–C$_8$)alkynyl, halo(C$_1$–C$_{12}$) alkyl, halo(C$_2$–C$_{12}$)alkenyl, halo(C$_2$–C$_{12}$)alkynyl, (C$_1$–C$_{12}$)alkoxy, (C$_1$–C$_{12}$)alkylthio, (C$_1$–C$_{12}$) alkylsulfonyl, (C$_1$–C$_{12}$)alkylsulfinyl, phenyl, phen (C$_1$–C$_{12}$)alkyl, phen(C$_2$–C$_{12}$)alkenyl, phen(C$_2$–C$_{12}$) alkynyl, cyano, halo(C$_1$–C$_{12}$)alkoxy, 1,3-dioxalan-2-yl, alkylenedioxy and nitro;

R$^3$ is a (C$_1$–C$_6$)alkyl, (C$_3$–C$_6$)alkenyl, (C$_3$–C$_6$)alkynyl, (C$_1$–C$_6$)alkoxy(C$_2$–C$_6$)alkyl, or silyl(C$_3$–C$_6$)alkynyl of the form (CH$_2$)$_n$C≡CSiR$^a$R$^b$R$^c$ wherein n is 1, 2, 3 or 4 and R$^a$, R$^b$, and R$^c$ are independently selected from (C$_1$–C$_6$)alkyl and phenyl; or is a (C$_1$–C$_6$)alkyl, (C$_3$–C$_6$)alkenyl, (C$_3$–C$_6$)alkynyl, (C$_1$–C$_6$)alkoxy (C$_2$–C$_6$)alkyl, or silyl(C$_3$–C$_6$)alkynyl of the form $(CH_2)_nC≡CSiR^aR^bR^c$ wherein n is 1, 2, 3 or 4 and $R^a$, $R^b$, and $R^c$ are independently selected from $(C_1-C_6)$alkyl and phenyl, wherein each of the foregoing groups is substituted with up to five halogen atoms;

$R^5$ is a hydrogen atom, $(C_1-C_6)$alkyl, $(C_3-C_6)$alkenyl, $(C_3-C_6)$alkynyl, $(C_1-C_6)$alkoxy, halo$(C_1-C_6)$alkyl, halo$(C_2-C_6)$alkenyl, halo$(C_2-C_6)$alkynyl, halo$(C_1-C_6)$alkoxy, $(C_1-C_6)$alkylthio, a halogen atom or cyano;

$R^6$ is a hydrogen atom, $(C_1-C_{12})$alkyl, cyclo$(C_3-C_7)$alkyl, $(C_2-C_{12})$alkenyl, $(C_2-C_{12})$alkynyl, halo$(C_1-C_6)$alkyl, halo$(C_2-C_6)$alkenyl, halo$(C_2-C_6)$alkynyl, tri$(C_1-C_6)$alkylsilyl$(C_2-C_{12})$alkynyl, cyano, $(C_6-C_{10})$aryl, ar$(C_1-C_4)$alkyl, $(C_4-C_5)$heterocyclyl, or $(C_6-C_{10})$aryl, ar$(C_1-C_4)$alkyl or $(C_4-C_5)$heterocyclyl substituted on the aryl portion with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, hen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, and nitro;

X and Y are both good leaving groups;

Z is fluoro, chloro or $OSO_2Rf$;

Rf is perfluoro$(C_1-C_{12})$alkyl or fluoro; and $R^6M$ is an organometallic reagent wherein M is selected from lithium, copper, aluminum, magnesium, zinc, tin, silicon, boron and combinations thereof.

2. The process of claim 1 which comprises the steps of (i) reacting an N-substituted amidine of formula I with an activated malonic acid derivative of formula II from about −40° C. to about −80° C. in the presence of an amine or an amide base and an ether, hydrocarbon, chlorinated hydrocarbon or a nitrile solvent or a mixture thereof to form a hydroxypyrimidinone compound of formula III, (ii) reacting the resulting hydroxypyrimidinone compound III with a compound of the formula $RfSO_2Z$ to form a sulfonyloxypyrimidinone compound of formula IV and (iii) reacting the resulting sulfonyloxypyrimidinone compound of formula IV with an organometallic reagent of the formula $R^6M$, in the presence or absence of catalysts, a base and other additives, at a temperature from about −80° C. to about 150° C. in a solvent or a mixture of solvents to form a pyrimidinone compound of formula V wherein Ar is furyl, naphthyl, phenyl, pyridyl, pyridyl salt or thienyl, or furyl, naphthyl, phenyl, pyridyl, pyridyl salt or thienyl substituted with up to three substituents independently-selected from bromo, chloro, fluoro, $(C_1-C_6)$alkyl, cyclo$(C_5-C6)$alkyl, $(C_2-C_6)$alkenyl, cyclo$(C_3-C_8)$alkenyl, $(C_2-C_6)$alkynyl, halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, $(C_1-C12)$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_6)$alkoxy, 1,3-dioxalan-2-yl, methylenedioxy, 1,2-ethylenedioxy and nitro;

$R^3$ is methyl, ethyl, n-propyl, $(C_3-C_4)$alkenyl, $(C_3-C_6)$alk-2-ynyl, $(C_1-C_2)$alkoxy$(C_2-C_3)$alkyl, 3-(trimethylsilyl)prop-2-ynyl, 3-(tert-butyldimethylsilyl)prop-2-ynyl or 3-(phenyldimethylsilyl)prop-2-ynyl, or is methyl, ethyl, n-propyl, $(C_3-C_4)$alkenyl, $(C_3-C_6)$alk-2-ynyl, $(C_1-C_2)$alkoxy$(C_2-C_3)$alkyl, 3-(trimethylsilyl)prop-2-ynyl, 3-(tert-butyldimethylsilyl)prop-2-ynyl or 3-(phenyldimethylsilyl)prop-2-ynyl wherein each of the foregoing groups is substituted with up to five halogen atoms;

$R^5$ is a hydrogen atom, chloro, fluoro, methyl, ethyl, n-propyl, isopropyl, allyl, prop-2-ynyl, $(C_1-C_2)$alkoxy, $(C_1-C_2)$alkylthio, halo$(C_1-C_2)$alkyl or halo$(C_1-C_2)$alkoxy;

$R^6$ is a hydrogen atom, $(C_1-C_6)$alkyl, cyclopropyl, cyclobutyl, cyclopentyl, $(C_2-C_6)$alkenyl, $(C_2-C_6)$alkynyl, halo$(C_1-C_3)$alkyl, halo$(C_2-C_6)$alkenyl, halo$(C_2-C_6)$alkynyl, tri$(C_1-C_6)$alkylsilyl$(C_2-C_{12})$alkynyl, cyano, phenyl, benzyl, 2-furyl, 3-furyl, 2-thienyl, 3-thienyl, 2-pyridyl, 3-pyridyl or 4-pyridyl, or phenyl, benzyl, 2-furyl, 3-furyl, 2-thienyl, 3-thienyl, 2-pyridyl, 3-pyridyl or 4-pyridyl substituted on the aryl portion with up to three substituents independently selected from bromo, chloro, fluoro, $(C_1-C_6)$alkyl, cyclo$(C_5-C_6)$alkyl, $(C_2-C_6)$alkenyl, cyclo$(C_3-C_8)$alkenyl, $(C_2-C_6)$alkynyl, halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_6)$alkoxy, 1,3-dioxalan-2-yl and nitro;

X and Y are independently selected from chloro, carboxylate and 1-imidazolyl;

Z is fluoro, chloro or $OSO_2Rf$;

Rf is perfluoro$(C_1-C_4)$alkyl or fluoro; and $R^6M$ is an organometallic reagent selected from $(R^6)_2CuCNLi_2$, $(R^6)_3B$ and $R^6SnR^xR^yR^z$ wherein $R^x$, $R^y$ and $R^z$ are alkyl.

3. The process of claims 1 or 2 wherein the base employed in step (i) is selected from triethylamine, N-methylmorpholine, lithium diisopropylamide and sodium bis(trimethylsilyl)amide.

4. The process of claim 3 wherein the base is sodium bis(trimethylsilyl)amide.

5. The process of claims 1 or 2 wherein the solvent employed in step (i) is selected from tetrahydrofuran, diethyl ether, dioxane, dimethoxymethane, toluene, dichloromethane and acetonitrile.

6. The process of claim 5 wherein the solvent is tetrahydrofuran.

7. The process of claims 1 or 2 wherein trifluoromethanesulfonic anhydride is the reactant employed in step (ii).

8. The process of claims 1 or 2 wherein the organometallic reagent employed in step (iii) is a higher order cuprate.

9. The process of claim 8 wherein the higher order cuprate is $(R^6)_2CuCNLi_2$.

10. The process of claim 8 wherein the reaction temperatures are from about −80° C. to about −40° C.

11. The process of claim 8 wherein tetrahydrofuran is the solvent.

12. The process of claims 1 or 2 wherein the organometallic reagent employed in step (iii) is a borane or tin compound.

13. The process of claim 12 wherein the catalyst used in step (iii) is a palladium or nickel compound.

14. The process of claim 13 wherein the palladium or nickel compound is selected from tetrakis (triphenylphosphine)palladium[0], [1,1'-bis (diphenylphosphino)ferrocene]palladium[II] chloride, tris (dibenzylldeneacetone)dipalladium[0], bis(benzonitrile) dichloropalladium[II], dichlorobis(triphenylphosphine) palladium[II] and [1,3-bis(diphenylphosphino)propane] nickel[II] chloride.

15. The process of claim 12 wherein the base used in step (iii) is selected from alkali metal carbonates, alkali metal phosphates, thallium carbonate and silver oxide.

16. The process of claim 12 wherein the additive used in step (iii) is lithium chloride or potassium bromide.

17. The process of claim 12 wherein the solvent used in step (iii) is selected from dioxane, tetrahydrofuran, diethyl ether, benzene, dimethylformamide and N-methyl-2-pyrrolidinone or mixtures thereof.

18. The process of claim 12 wherein the reaction temperature in step (iii) is from about 20° C. to about 150° C.

19. The process of claim 2 wherein

Ar is 2-furyl, 3-furyl, 4-chloro-2-furyl, 5-chloro-2-furyl, 5-chloro-3-furyl, 2,5-dichloro-3-furyl, 2-naphthyl, phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl, 2-pyridyl, 4-chloro-2-pyridyl, 6-chloro-2-pyridyl, 4,6-dichloro-2-pyridyl, 3-pyridyl, 5-bromo-3-pyridyl, 5,6-dichloro-3-pyridyl, 5-chloro-3-pyridyl, 5-fluoro-3-pyridyl, 4-pyridyl, 2-fluoro-4-pyridyl, 2-chloro-4-pyridyl, 2-chloro-6-methyl-4-pyridyl, 2-methyl-4-pyridyl, 2-methoxy-4-pyridyl, 2-cyano-4-pyridyl, 2,6-difluoro-4-pyridyl, 6-dichloro-4-pyridyl, 2-thienyl, 3-thienyl, 4-chloro-2-thienyl, 5-chloro-2-thienyl, 5-chloro-3-thienyl, 2,5-dichloro-3-thienyl or 3,4-methylenedioxyphenyl;

$R^3$ is ethyl, allyl, 3-chloroallyl, prop-2-ynyl, but-2-ynyl, pent-2-ynyl or 2-methoxyethyl;

$R^5$ is methyl, ethyl, methoxy, methylthio, difluoromethoxy or trifluoromethoxy; and $R^6$ is methyl, ethyl, n-propyl, n-butyl, n-pentyl, n-hexyl, sec-butyl, isopropyl, isobutyl, vinyl, isopropenyl, allyl, ethynyl, prop-1-ynyl, 1-methylprop-2-ynyl, prop-2-ynyl, trifluoromethyl, pentafluoroethyl, trichloromethyl, bromomethyl, chloromethyl, difluoromethyl, chlorodifluoromethyl, phenyl or 3-thienyl.

20. A process for making the pyrimidinone compound of formula V

which comprises the steps of
(i) reacting an N-substituted amidine of formula I with an activated malonic acid derivative of formula II at room temperature or below in the presence of a base and a solvent or solvent mixture to form a hydroxypyrimidinone compound of formula III

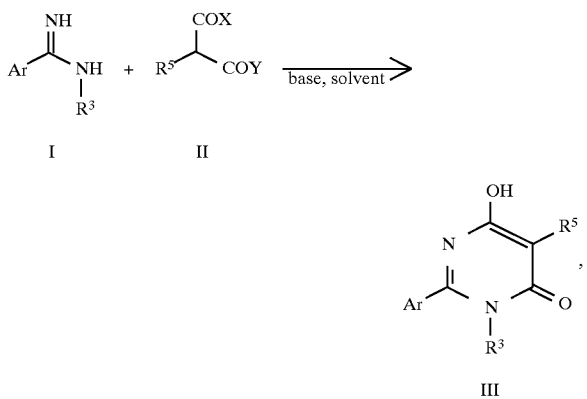

(ii) reacting the resulting hydroxypyrimidinone compound of formula III with a compound of the formula $RfSO_2Z$ to form a sulfonyloxypyrimidinone compound of formula IV

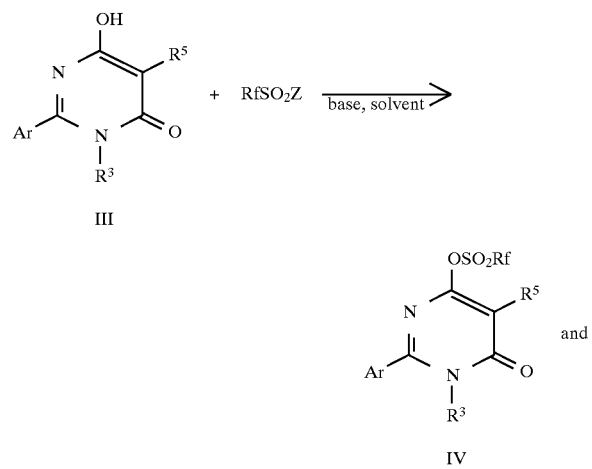

(iii) reacting the resulting sulfonyloxypyrimidinone compound of formula IV with a 1-alkynyl reagent of the formula $R^6H$, in the presence of a catalyst and a base, at a temperature from about 20° C. to about 150° C. in a solvent or mixture of solvents to form a pyrimidinone compound of formula V wherein Ar is a $(C_6-C_{10})$aryl or $(C_4-C_5)$heteroaromatic group, or a $(C_6-C_{10})$aryl or $(C_4-C_5)$heteroaromatic group substituted with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_{12})$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-Cl_2)$alkyl, phen$(C_2-C_{12})$alkenyl, phen$(C_2-C_{12})$alkynyl, cyano, halo$(C_1-C_{12})$alkoxy, 1,3-dioxalan-2-yl, alkylenedioxy and nitro;

$R^3$ is a $(C_1-C_6)$alkyl, $(C_3-C_6)$alkenyl, $(C_3-C_6)$alkynyl, $(C_1-C_6)$alkoxy$(C_2-C_6)$alkyl, or silyl$(C_3-C_6)$alkynyl of the form $(CH_2)_nC\equiv CSiR^aR^bR^c$ wherein n is 1, 2, 3 or 4 and $R^a$, $R^b$, and $R^c$ are independently selected from $(C_1-C_6)$alkyl and phenyl; or is a $(C_1-C_6)$alkyl, ($C_3$–$C_6$)alkenyl, ($C_3$–$C_6$)alkynyl, ($C_1$–$C_6$)alkoxy ($C_2$–$C_6$)alkyl, or silyl($C_3$–$C_6$)alkynyl of the form $(CH_2)_nC{\equiv}CSiR^aR^bR^c$ wherein n is 1, 2, 3 or 4 and $R^a$, $R^b$, and $R^c$ are independently selected from ($C_1$–$C_6$)alkyl and phenyl, wherein each of the foregoing groups is substituted with up to five halogen atoms;

$R^5$ is a hydrogen atom, ($C_1$–$C_6$)alkyl, ($C_3$–$C_6$)alkenyl, ($C_3$–$C_6$)alkynyl, ($C_1$–$C_6$)alkoxy, halo($C_1$–$C_6$)alkyl, halo($C_2$–$C_6$)alkenyl, halo($C_2$–$C_6$)alkynyl, halo($C_1$–$C_6$)alkoxy, ($C_1$–$C_6$)alkylthio, a halogen atom or cyano;

$R^6$ is a ($C_2$–$C_{12}$)alkyn-1-yl, halo($C_2$–$C_6$)alkyn-1-yl or tri($C_1$–$C_6$)alkylsilyl($C_2$–$C_{12}$)alkyn-1-yl;

X and Y are both good leaving groups;

Z is fluoro, chloro or $OSO_2Rf$; and

Rf is perfluoro($C_1$–$C_{12}$)alkyl or fluoro.

21. The process of claim 20 wherein the alkyne $R^6H$ is (trimethylsilyl)acetylene used in step (iii).

22. The process of claim 21 wherein the catalyst is dichlorobis(triphenylphosphine)palladium[II], the base is triethylamine and the solvent is dimethylformamide.

23. A process for making the pyrimidinone compound of formula V

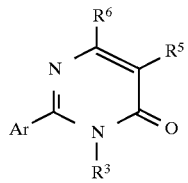

V wherein $R^3$ is $(CH_2)_nC{\equiv}CH$ or $(CH_2)_nCCSiR^aR^bR^c$, n is 1, 2, 3 or 4 and $R^a$, $R^b$, and $R^c$ are independently selected from ($C_1$–$C_6$)alkyl and phenyl; which comprises the steps of (i) reacting an N-substituted amidine of formula I with an activated malonic acid derivative of formula II at room temperature or below in the presence of a base and a solvent or solvent mixture to form a hydroxypyrimidinone compound of formula III

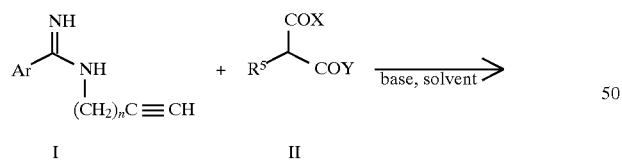

I     II

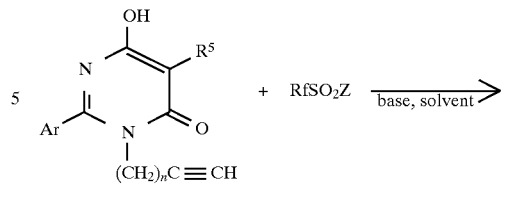

III (ii) reacting the resulting hydroxypyrimidinone compound of formula III with a compound of the formula $RfSO_2Z$ to form a sulfonyloxypyrimidinone compound of formula IV

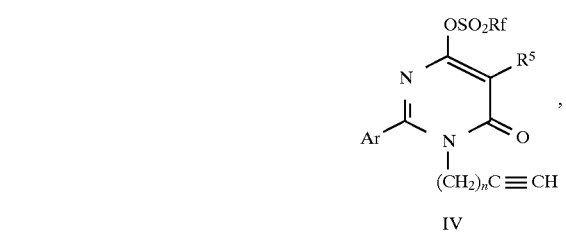

IV (iia) reacting the resulting sulfonyloxypyrimidinone compound of formula IV with a silylating agent of the formula $R^aR^bR^cSiY'$, wherein $R^a$, $R^b$ and $R^c$ are independently selected from ($C_1$–$C_6$)alkyl and phenyl and Y' is a good leaving group, in the presence of a base to form a compound of formula IVa

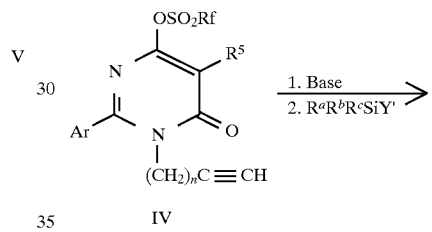

IV

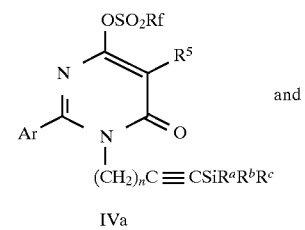

IVa (iii) reacting the resulting sulfonyloxypyrimidinone compound of formula IVa with an organometallic reagent of the formula $R^6M$, in the presence or absence of catalysts, a base and other additives, at a temperature from about −80° C. to about 150° C. in a solvent or mixture of solvents to form a pyrimidinone compound of formula V wherein $R^3$ is $(CH2)_nC{\equiv}CSiR^aR^bR^c$, followed by a desilylation, if desired, to form a pyrimidinone compound of formula V wherein $R^3$ is $(CH2)_nC{\equiv}CH$ and wherein Ar is a ($C_6$–$C_{10}$)aryl or ($C_4$–$C_5$)heteroaromatic group, or a ($C_6$–$C_{10}$)aryl or ($C_4$–$C_5$)heteroaromatic group substituted with up to three substituents independently selected from bromo, chloro, fluoro, ($C_1$–$C_{12}$) alkyl, cyclo($C_3$–$C_8$)alkyl, ($C_2$–$C_{12}$)alkenyl, cyclo ($C_3$–$C_8$)alkenyl, ($C_2$–$C_{12}$)alkynyl, halo($C_1$–$C_{12}$) alkyl, halo($C_2$–$C_{12}$)alkenyl, halo($C_2$–$C_{12}$)alkynyl, ($C_1$–C12)alkoxy, ($C_1$–C12)alkylthio, ($C_1$–$C_{12}$) alkylsulfonyl, ($C_1$–$C_{12}$)alkylsulfinyl, phenyl, phen ($C_1$–$C_{12}$)alkyl, phen($C_2$–$C_{12}$)alkenyl, phen($C_2$–$C_{12}$) alkynyl, cyano, halo($C_1$–$C_{12}$)alkoxy, 1,3-dioxalan-2-yl, alkylenedioxy and nitro;

$R^5$ is a hydrogen atom, $(C_1-C_6)$alkyl, $(C_3-C_6)$alkenyl, $(C_3-C6)$alkynyl, $(C_1-C_6)$alkoxy, halo$(C_1-C_6)$alkyl, halo$(C_2-C_6)$alkenyl, halo$(C_2-C_6)$alkynyl, halo$(C_1-C_6)$alkoxy, $(C_1-C_6)$alkylthio, a halogen atom or cyano;

$R^6$ is a hydrogen atom, $(C_1-C_{12})$alkyl, cyclo$(C_3-C_7)$alkyl, $(C_2-C_{12})$alkenyl, $(C_2-C_{12})$alkynyl, halo$(C_1-C_6)$alkyl, halo$(C_2-C_6)$alkenyl, halo$(C_2-C_6)$alkynyl, tri$(C_1-C_6)$alkylsilyl$(C_2-C_{12})$alkynyl, cyano, $(C_6-C_{10})$aryl, ar$(C_1-C_4)$alkyl, $(C_4-C_5)$heterocyclyl, or $(C_6-C_{10})$aryl, ar$(C_1-C_4)$alkyl or $(C_4-C_5)$heterocyclyl substituted on the aryl portion with up to three substituents independently selected from bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, halo$(C_2-C_{12})$alkenyl, halo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C12)$alkenyl, phen$(C_2-C_{12})$alkynyl, cyano, halo$(C_1-C_{12})$alkoxy, 1,3-dioxalan-2-yl, and nitro;

X and Y are both good leaving groups;

Z is fluoro, chloro or $OSO_2Rf$;

Rf is perfluoro$(C_1-C_{12})$alkyl or fluoro; and $R^6M$ is an organometallic reagent wherein M is selected from lithium, copper, aluminum, magnesium, zinc, tin, silicon, boron and combinations thereof.

24. The process of claim 23 wherein

Ar is furyl, naphthyl, phenyl, pyridyl, pyridyl salt or thienyl, or furyl, naphthyl, phenyl, pyridyl, pyridyl salt or thienyl substituted with up to three substituents independently selected from bromo, chloro, fluoro, $(C_1-C_6)$alkyl, cyclo$(C_5-C_6)$alkyl, $(C_2-C_6)$alkenyl, cyclo$(C_3-C_8)$alkenyl, $(C_2-C_6)$alkynyl, halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, $(C_1-C_{12})$alkylsulfonyl, $(C_{12}-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_6)$alkoxy, 1,3-dioxalan-2-yl, methylenedioxy, 1,²-ethylenedioxy and nitro;

$R^5$ is a hydrogen atom, chloro, fluoro, methyl, ethyl, n-propyl, isopropyl, allyl, prop-2-ynyl, $(C_1-C_2)$alkoxy, $C_1-C_2)$alkylthio, halo$(C_1-C_2)$alkyl or halo$(C_1-C_2)$alkoxy; and $R^6$ is a hydrogen atom, $(C_1-C_6)$alkyl, cyclopropyl, cyclobutyl, cyclopentyl, $(C_2-C_6)$alkenyl, $(C_2-C_6)$alkynyl, halo$(C_1-C_3)$alkyl, halo$(C_2-C_6)$alkenyl, halo$(C_2-C_6)$alkynyl, tri$(C_1-C_6)$alkylsilyl$(C_2-C_{12})$alkynyl, cyano, phenyl, benzyl, 2-furyl, 3-furyl, 2-thienyl, 3-thienyl, 2-pyridyl, 3-pyridyl or 4-pyridyl, or phenyl, benzyl, 2-furyl, 3-furyl, 2-thienyl, 3-thienyl, 2-pyridyl, 3-pyridyl or 4-pyridyl substituted oh the aryl portion with up to three substituents independently selected from bromo, chloro, fluoro, $(C_1-C_6)$alkyl, cyclo$(C_5-C_6)$alkyl, $(C_2-C_6)$alkenyl, cyclo$(C_3-C_8)$alkenyl, $(C_2-C_6)$alkynyl, halo$(C_1-C_6)$alkyl, halo$(C_2-C_6)$alkenyl, halo$(C_2-C_6)$alkynyl, $(C_1-C_6)$alkoxy, $(C_1-C_6)$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_6)$alkoxy, 1,3-dioxalan-2-yl and nitro.

25. The process of claims 23 or 24 wherein the base is an alkyllithium, an alkylmagnesium halide or an alkali metal amide and Y' is chloro or trifluoromethanesulfonyloxy.

\* \* \* \* \*